(12) United States Patent
Ozenne (10) Patent No.: US 10,213,568 B2
(45) Date of Patent: Feb. 26, 2019

(54) NASOPHARYNGEAL CANNULA FOR SIDE-STREAM CAPNOGRAPHY (71) Applicant: Deltamedics, Gouvieux (FR)

(72) Inventor: Jean-Christophe Ozenne, Gouvieux (FR)

(73) Assignee: Deltamedics, Gouvieux (FR)

( * ) Notice: Subject to any disclaimer, the term of this patent is extended or adjusted under 35 U.S.C. 154(b) by 410 days.

(21) Appl. No.: 14/776,479

(22) PCT Filed: Mar. 13, 2014

(86) PCT No.: PCT/EP2014/054942
§ 371 (c)(1),
(2) Date: Sep. 14, 2015

(87) PCT Pub. No.: WO2014/140163
PCT Pub. Date: Sep. 18, 2014

(65) Prior Publication Data
US 2016/0022941 A1 Jan. 28, 2016

(30) Foreign Application Priority Data
Mar. 15, 2013 (FR) ...................................... 13 52333

(51) Int. Cl.
*A61M 16/04* (2006.01)
*A61M 16/08* (2006.01)
(Continued)

(52) U.S. Cl.
CPC ....... *A61M 16/0461* (2013.01); *A61B 5/0836* (2013.01); *A61B 5/097* (2013.01); *A61M 16/0477* (2014.02); *A61M 16/0484* (2014.02); *A61M 16/0486* (2014.02); *A61M 16/0488* (2013.01); *A61M 16/085* (2014.02);
(Continued)

(58) Field of Classification Search
CPC ..... A61B 5/097; A61B 5/0836; A61B 5/0086; A61M 16/0666; A61M 16/085; A61M 16/0683; A61M 2202/0208; A61M 2202/0014; A61M 16/0461; A61M 16/0488; A61M 16/0486; A61M 16/0477; A61M 16/0463; A61M 2230/432
See application file for complete search history.

(56) References Cited

U.S. PATENT DOCUMENTS

4,821,715 A * 4/1989 Downing .......... A61M 16/0666
128/200.26
6,098,617 A * 8/2000 Connell ................ A61M 16/04
128/200.26
(Continued)

*Primary Examiner* — Steven O Douglas
(74) *Attorney, Agent, or Firm* — Christensen O'Connor Johnson Kindness PLLC (57) ABSTRACT

A nasopharyngeal cannula comprising a body formed by a tubular portion that is curved so as to be inserted into a patient's nostril and a collar for resting on the base of the patient's nostril is described. The cannula also comprises a main channel forming a fluid passage between the collar and the tubular portion of the body and two auxiliary channels formed in the body and extending from the collar into the main channel. Each auxiliary channel opens into the collar at an inlet/outlet port oriented radially in relation to the axis of the main channel such as to be oriented laterally on each side of the patient's nostril when the cannula is in place on the patient.

17 Claims, 4 Drawing Sheets

(51) Int. Cl.
*A61B 5/083* (2006.01)
*A61B 5/097* (2006.01)

(52) U.S. Cl.
CPC . *A61M 16/0463* (2013.01); *A61M 2202/0208* (2013.01); *A61M 2230/432* (2013.01)

(56) References Cited

U.S. PATENT DOCUMENTS

| | | | | |
|---|---|---|---|---|
| 6,394,093 | B1* | 5/2002 | Lethi | A61M 16/0461 128/207.13 |
| 6,422,240 | B1* | 7/2002 | Levitsky | A61B 5/083 128/204.18 |
| 7,278,420 | B2* | 10/2007 | Ganesh | A61M 16/04 128/200.26 |
| 2008/0110456 | A1* | 5/2008 | Flynn | A61M 16/0488 128/200.26 |
| 2008/0308108 | A1* | 12/2008 | Diorio | A61M 16/0461 128/207.14 |
| 2012/0080037 | A1* | 4/2012 | Guyuron | A61M 16/0461 128/207.18 |
| 2016/0029923 | A1* | 2/2016 | Ozenne | A61M 16/04 600/473 |

* cited by examiner

NASOPHARYNGEAL CANNULA FOR SIDE-STREAM CAPNOGRAPHY

The invention relates to a device for clearing the airways of a patient, more particularly a nasopharyngeal cannula permitting an injection of dioxygen and a capnographic measurement.

A cannula is a straight or curved, flexible or rigid tube which permits the passage of a fluid such as air or a liquid through an orifice. A nasopharyngeal cannula is used in medicine to keep open the airways of an unconscious patient, for example a patient who is under anesthesia or a patient who is in a coma, and more particularly to maintain the permeability of the airways with the hypopharynx and to facilitate the removal of tracheobronchial secretions.

A nasopharyngeal cannula is generally in the form of a flexible tube made of plastic and in two parts.

A first part is curved slightly and flexible, or semi-rigid, so as to follow the trajectory of the nasal cavity as far as the pharynx and to thus clear a channel as far as the pharynx. The free end of the first part is positioned behind the base of the tongue, above the epiglottis. In this way, a passage of air is maintained toward the lungs.

A second part comprises a collar, which rests on the entrance to the patient's nostril once the cannula is in place and which avoids any excessive forward movement of the cannula.

There are several sizes of nasopharyngeal cannula. The sizes vary between children and adults. Their size is expressed mainly as a function of the internal diameter of the cannula.

During an operation under anesthesia, a face mask is generally used in order to inject dioxygen into the patient via the conduit of the nasopharyngeal cannula. However, the use of a mask impedes access to the patient's face, if this is necessary.

In addition, the use of a mask gives rise to complex positioning in order to be able to carry out capnography of the air exhaled by the patient.

Capnography is a measurement of the concentration or partial pressure of carbon dioxide in the air exhaled by a patient. Measurements of this type are commonly used on patients under anesthesia. The presence of carbon dioxide in the air exhaled over several exhalations by a patient who has just been intubated makes it possible in particular to confirm that the endotracheal tube is properly placed in the trachea.

Capnography also makes it possible to obtain an indirect measurement of the partial pressure of carbon dioxide in the arterial blood. This information makes it possible to evaluate the state of vascularization of the patient. Capnography reflects directly the capacity of the patient's lungs to eliminate carbon dioxide, and it reflects indirectly the production of carbon dioxide by the tissues and its transport as far as the lungs.

It makes it possible to detect, very early on, signs of respiratory deficiency such as hypoventilation, or disconnection of a circuit or tube in the esophagus. During an operation under anesthesia, capnography makes it possible to provide information such as the frequency and regularity of ventilation, which is more useful than the information provided by an oximeter.

It provides a method for rapid detection of critical conditions, such as a badly positioned tracheal tube, a ventilation defect, or a circulatory defect, and for prevention of irreversible complications.

In order to carry out both injection of dioxygen and collection of the gases exhaled by the patient, so as to perform a measurement of the level of carbon dioxide, without using a cumbersome face mask, the document US 2007/0095347 discloses a suitable nasopharyngeal device.

However, such a device does not use a nasopharyngeal cannula, so that the airways may be obstructed, which means it is not possible to guarantee optimal injection of oxygen and collection of carbon dioxide under the best possible conditions.

Furthermore, the device used is heavy and very bulky in the area of the patient's nose, and it has a complex harness for fitting on the patient.

The document US 2008/0000481 furthermore discloses an oropharyngeal device of suitable shape which is designed to be inserted into a patient's mouth. The device comprises a body having at least two channels which extend through the body in order to form two air passages through which, firstly, dioxygen can be injected, and, secondly, carbon dioxide can be removed. The channels are formed in the body of the device, which comprises a collar on the proximal portion in order to prevent the device from being introduced too far into the mouth.

These uniquely oropharyngeal devices do not have means for easily and quickly securing them on the patient, which means allow them to be maintained on the patient once the device has been fitted in the patient's mouth, whilst permitting rapid removal of the device if the patient wakes up or if intubation is necessary.

There is also known from documents US 2007/267024, US 2008/308108, U.S. Pat. No. 4,821,715 and EP 1 188 457 an oropharyngeal or nasopharyngeal device which is designed to form a passage for gas to be inhaled, in which there is accommodated a pair of conduits which are designed to be slid into the inner passage(s) in order to inject dioxygen, in particular over a proximal portion, and to collect exhaled gas, in particular over a distal portion, in order to measure the level of $CO_2$.

These devices also do not have means for easily and quickly securing them on the patient, which means allow them to be maintained on the patient once the device has been fitted in the patient's mouth or nose, whilst permitting rapid removal of the device if the patient wakes up or if intubation is necessary.

Moreover, these devices have the disadvantage of being in several parts, namely a part composed of the cannula, and a part composed of the injection and extraction tubes to be inserted. The additional assembly time may be critical, in particular in an emergency situation.

An oropharyngeal or nasopharyngeal cannula has to be fitted and secured on the patient in such a way that he is able to remove it when necessary, especially when the patient wakes up. The securing of the cannula makes it possible to hold the device in position, but this securing must be easily removable.

A nasopharyngeal cannula is most often put in place during the period of recovery after anesthesia, in order to facilitate clearance of the bronchi, and also in cases where the patient is semi-conscious. Although a nasopharyngeal cannula is generally better tolerated by a patient than an oropharyngeal cannula of the Guedel type, some patients may feel a degree of discomfort that may lead to the nasopharyngeal cannula being removed urgently.

The document U.S. Pat. No. 3,802,431 also discloses a nasal cannula for injecting dioxygen into the nostrils of a patient. The device is composed of a small cannula placed at the entrance to each nostril in order to inject dioxygen into each nostril with the aid of tubes that are connected to the cannulas and are sufficiently flexible to be passed behind the patient's ears once the device is in place on the patient.

However, such a device does not have a nasopharyngeal cannula and only permits the injection of a fluid at the entrance to the nostrils.

The object of the invention is to eliminate the aforementioned disadvantages by making available a nasopharyngeal cannula which is designed to be secured on the patient, in particular with the aid of the tubes for injection/extraction, and to keep the cannula in place on the patient.

According to one aspect of the invention, a nasopharyngeal cannula is proposed comprising a body formed by a tubular portion that is curved so as to be inserted into a patient's nostril, and by a collar that is able to rest on the base of the patient's nostril, the cannula comprising a main conduit forming a fluid passage between the collar and the tubular portion of the body, and two auxiliary conduits which are formed in the body and extend from the collar into the main conduit.

The base of the patient's nostril comprises the columella and the wing of the nostril.

According to a general feature of the invention, each auxiliary conduit opens into the collar at an input/output orifice oriented radially with respect to the axis of the main conduit so as to be oriented laterally on each side of the patient's nostril when the cannula is fitted on the patient.

By thus orienting the input/output orifices, the injection/extraction tubes, which are coupled to the input/output orifices, extend in the direction of the patient's ears, on each side of the patient's nostrils. In this way, each injection/extraction tube can be passed behind an ear in order to secure the nasopharyngeal cannula on the patient such that it is easily removable.

Preferably, the direction between each input/output orifice and the axis of the main conduit forms an angle of between −10° and 20°, more particularly between 0° and 10°, with an axis orthogonal to the axis of the patient's nose when the cannula is fitted on the patient.

An angle of between −10 and 20°, particularly an angle of about 0°, makes it possible to direct the injection/extraction tubes toward the upper edge of the ears, thus making it easier to pass the tubes behind the ears.

According to one embodiment, the collar can comprise a first and a second input/output bend, each one opening into an input/output orifice. In this embodiment, each auxiliary conduit passes through the collar into the input/output bend. The collar can have any thickness. The input/output bends protrude from the surface of the collar.

According to an alternative, each auxiliary conduit can comprise a portion formed radially in the collar, the input/output orifice being arranged radially on the collar. In this alternative, the thickness of the collar must have a thickness sufficient to permit the passage of the auxiliary conduits.

Preferably, in this alternative, each input/output orifice arranged radially on the collar is connected to an auxiliary conduit via the portion of the auxiliary conduit extending radially in the collar, forming an angle of between 0° and 20°, more particularly an angle of about 10°, with the plane defined by the surface of the collar, so as to orient the corresponding input/output orifice toward the patient's face.

This angle makes it possible to orient the injection/extraction tubes, which are coupled to the input/output orifices, so as to keep them as close as possible to the patient's face, and thus to reduce the risks of an element or a tool getting caught in the injection/extraction tubes.

Advantageously, the nasopharyngeal cannula can comprise two flexible injection/extraction tubes which are able to be passed behind the patient's ears when the cannula is fitted on the patient, a first end of each tube being connected to an input/output orifice.

The tubes can be connected to the input/output orifices in a removable manner, or securely and non-removably. The presence of the integral tubes on the oropharyngeal cannula makes it possible to avoid any assembly operation apart from the connection of the free ends of the tubes to extraction means, such as a capnograph, or to injection means during the fitting of the cannula on the patient.

The nasopharyngeal cannula can advantageously comprise a clamping ring which is able to hold the two tubes together and can slide along the two tubes so as to hold the cannula in place when it is fitted on the patient and each tube passes behind an ear.

Once the tubes have been passed behind each ear, the clamping ring makes it possible to clamp the tube under the chin by lifting the clamping ring toward the chin. This makes it possible to securely fasten the cannula, while at the same time making it possible to quickly remove the cannula if necessary.

Advantageously, a second end of the injection/extraction tubes can comprise means for connection to injection or extraction appliances.

The connection means can be specific connectors which are dedicated to appliances for measurement or injection of gas. By having a specific connector for each tube, the risks of connection error are zero, even in an emergency situation, since each connector is dedicated to a specific appliance.

Preferably, the first auxiliary conduit is intended for injecting dioxygen into the patient's airways, and the second auxiliary conduit is intended for extracting gases exhaled by the patient so as to perform a capnographic measurement. For this purpose, the first auxiliary conduit comprises an input orifice connected to an injection tube for injecting dioxygen into the patient's airways, and the second auxiliary conduit comprises an output orifice, which is connected to an extraction tube for extracting gases exhaled by the patient so as to perform a capnographic measurement.

The tubular portion preferably comprises a free end and a proximal part, and the first auxiliary conduit extends as far as a proximal part of the tubular portion, and the second conduit extends as far as a distal part comprising the free end of the tubular portion.

By separating the locations where the auxiliary conduits open into the main conduit, the disturbances which are associated in particular with the turbulence created by the injection of dioxygen are reduced for the extraction of the gases exhaled by the patient, and the carbon dioxide measurement offers a better ratio of signal to noise. According to empirical measurements and fluid mechanics, it is preferable to carry out extraction of the exhaled gases in an area which is more distal than that for the injection of oxygen, in order for there to be less disruption by the flow of oxygen.

In one variant, it is also possible to have two tubes for collection of carbon dioxide which are coupled to the two input/output orifices, the two tubes being coupled to a single capnography device. In this way, the device can be used only for sampling of the carbon dioxide. In this configuration, the two auxiliary conduits can open into the main conduit at locations which are similar or separate. Likewise, the nasopharyngeal cannula can be used only for the injection of dioxygen via the two auxiliary conduits.

Preferably, the first auxiliary conduit is formed in an upper wall of the tubular portion of the body, and the second auxiliary conduit is formed in a lower wall of the tubular portion of the body.

By forming the second auxiliary conduit in the lower wall of the tubular portion, the risks of occlusion by secretions, such as mucus and saliva, are reduced. Indeed, when the patient is lying on his back, the lower surface of the distal wall of the nasopharyngeal cannula, fitted in the patient's nose as far as his pharynx, is raised in the area of the free end near the back of the pharynx where the secretions can accumulate.

At least one of the two auxiliary conduits can advantageously comprise a cross section of oblong shape, at least on the tubular portion of the body.

In this way, the volume of fluid, in particular gaseous fluid, that can be conveyed through the conduit is greater than in the case of a conduit with a cylindrical cross section. The oblong cross sections can be made to follow the contours of the main conduit of the nasopharyngeal cannula. In this way, curved oblong cross sections are obtained, which makes it possible to form the auxiliary conduits in the walls of the cannula without having to substantially increase the thickness of the walls of the body of the cannula. This can be done while maintaining a substantial volume of transferred gas.

Advantageously, the cannula can comprise at least one additional conduit which is formed in the body and extends from the collar as far as at least the tubular portion of the body. The additional conduit can be designed for aspiration of secretions in the patient's pharynx, so as to prevent the airways from being obstructed by these secretions. The secretions can also be aspirated via a tube inserted into the main conduit.

Advantageously, at least one of the auxiliary conduits comprises an orifice which opens into the main conduit and has a frustoconical shape with a larger cross section than the mean cross section of the auxiliary conduit.

The frustoconical shape of the orifice that opens into the main conduit at the level of the tubular portion of the body makes it possible to assist the good distribution of the dioxygen injected in one case, and to optimize the sampling of carbon dioxide in another case.

Preferably, the free end of the tubular portion of the body has a rounded shape. The rounded shape of the free end makes it possible to reduce the risks of injury when inserting the nasopharyngeal cannula, especially compared to a nasopharyngeal cannula that has a beveled free end.

The body can be made of flexible and sliding plastic. In this way, the nasopharyngeal cannula can be inserted without using a lubricating gel.

Figure 1:
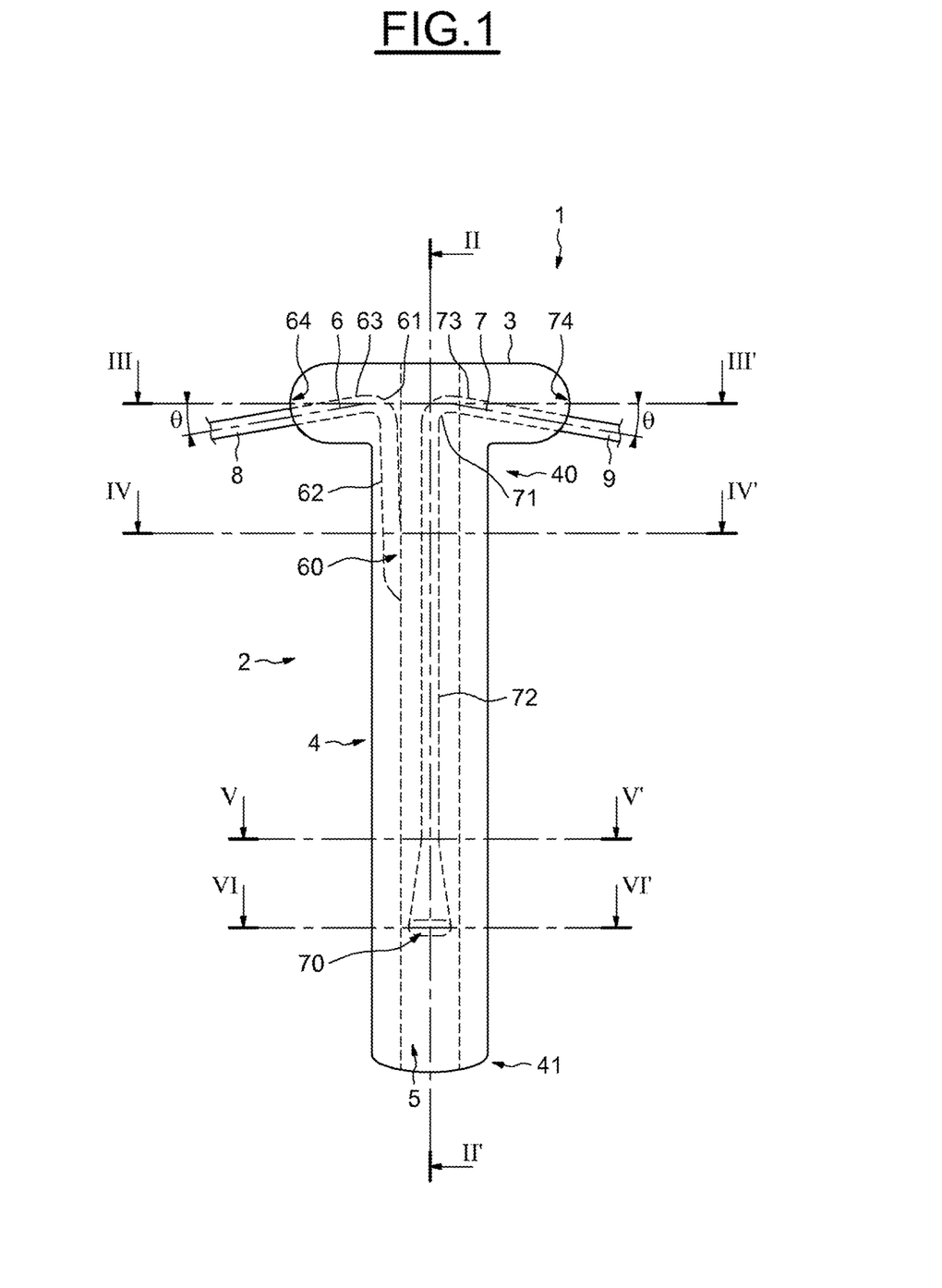
FIG. 1 shows a schematic view, from below, of a nasopharyngeal cannula according to an embodiment of the invention.

Other advantages and features of the invention will become clear from examination of the detailed description of a non-limiting embodiment and from the attached drawings, in which:

FIG. 1 shows a schematic view, from below, of a nasopharyngeal cannula 1 according to an embodiment of the invention.

The nasopharyngeal cannula 1 comprises a body 2 made of flexible sliding plastic, for example medical PVC, and formed with a collar 3 and a tubular portion 4. As is illustrated in FIG. 2, which shows the cannula 1 from FIG. 1 in longitudinal section in the plane II-II', the tubular portion 4 has a curved shape so as to permit the insertion of the nasopharyngeal cannula 1, and in particular its tubular portion 4, into a patient's nostril as far as his pharynx, in such a way as to pass behind the base of the tongue and thereby keep the pharynx open.

The collar 3 is intended to rest on the outside of the base of the patient's nostril once the cannula 1 has been inserted into the patient's nostril. The body 2 comprises a main conduit 5 extending from the collar 3 as far as the free end 41 of the tubular portion 4. The main conduit 5 thus forms a fluid passage between the collar 3 and the tubular portion 4 of the body 2 of the nasopharyngeal cannula 1. Once the cannula 1 has been fitted on the patient, the main conduit 5 forms a fluid passage between the pharynx and the nostril of the patient.

Figure 2:
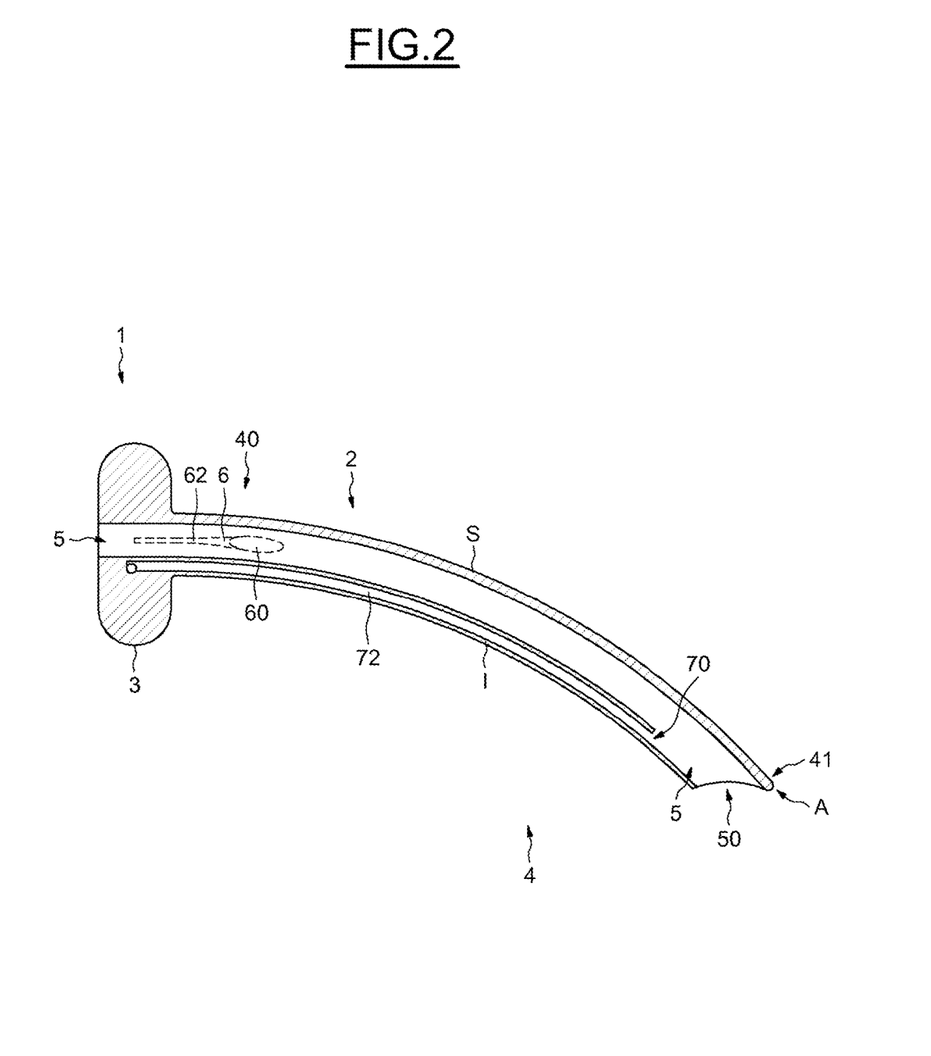
FIG. 2 shows a sectional view of the nasopharyngeal cannula from FIG. 1 in a longitudinal plane II-II'.

As is shown in FIGS. 1 and 2, the nasopharyngeal cannula 1 comprises a first auxiliary conduit 6 formed within the thickness of the body 2 separating the main conduit 5 from the outside of the body 2. The first auxiliary conduit 6 extends from the collar 3 as far as a proximal part 40 of the tubular portion 4. It opens into the main conduit 5 via a first opening 60, as is shown in FIGS. 1 and 3, and also in FIG. 4 which shows a view of the nasopharyngeal cannula 1 from FIG. 1 in the sectional plane IV-IV'.

Figure 3:
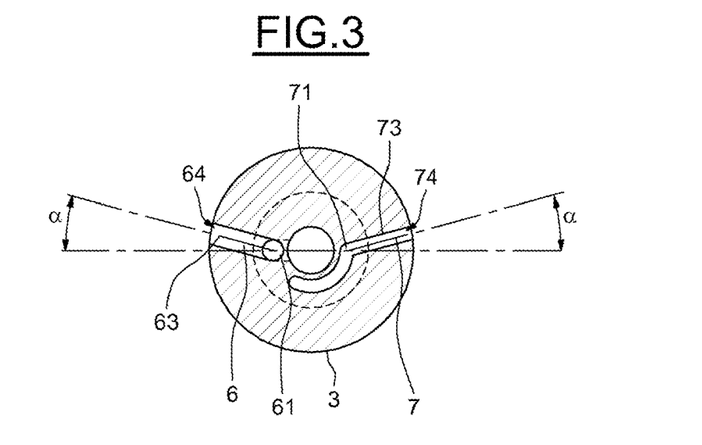
FIG. 3 shows a sectional view of the nasopharyngeal cannula from FIG. 1 in a transverse plane III-III'.
Figure 4:
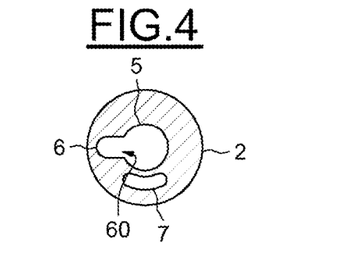
FIG. 4 shows a sectional view of the nasopharyngeal cannula from FIG. 1 in a transverse plane IV-IV'.
Figure 5:
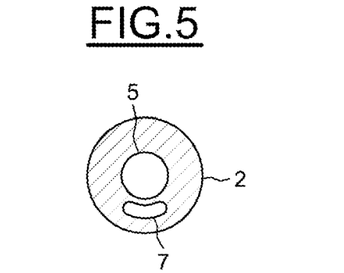
FIG. 5 shows a sectional view of the nasopharyngeal cannula from FIG. 1 in a transverse plane V-V'.

As is shown in FIG. 1 and also in FIG. 3, which shows the nasopharyngeal cannula 1 from FIG. 1 in a sectional view in the plane III-III', the first auxiliary conduit 6 comprises a bend 61 which connects a first portion 62 of the first auxiliary conduit 6, extending parallel to the longitudinal axis II-II' as far as the first opening 60, and a second portion 63 of the first auxiliary conduit 6 extending in the collar 3. The second portion 63 extends in the collar 3 in a radial direction with respect to the longitudinal axis II-II', comparable to the axis of the main conduit 5, as far as an input orifice 64.

The nasopharyngeal cannula 1 comprises a second auxiliary conduit 7 likewise formed within the thickness of the body 2 and having a curved oblong shape in cross section. The second auxiliary conduit 7 passes through the body 2 from the collar 3 and opens into the main conduit 5 via a second opening 70 which is arranged upstream from the free end 41 of the tubular portion 4, as is shown in FIGS. 1 and 2, and also in FIG. 6 which shows a view of the nasopharyngeal cannula 1 from FIG. 1 in the sectional plane VI-VI'. By thus positioning the second opening 70 upstream from the free end 41 of the tubular portion, the risks of the second opening 70 being obstructed by secretions in the throat is reduced.

Figure 6:
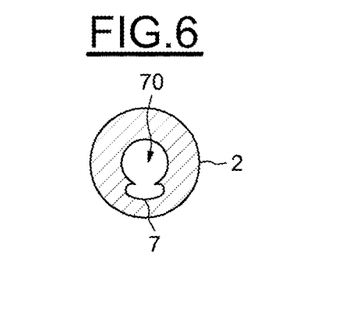
FIG. 6 shows a sectional view of the nasopharyngeal cannula from FIG. 1 in a transverse plane VI-VI'.

These risks are further limited by the choice of forming the second auxiliary conduit 70 in the lower wall I of the tubular portion 4. In fact, when the patient is lying on his back, the lower wall I of the tubular portion 4 of the nasopharyngeal cannula 1 fitted in the patient's nose is raised in the area of the free end 41 near the back of the pharynx where the secretions can accumulate.

In order to further reduce the possible accumulation of secretions in the pharynx, the nasopharyngeal cannula 1 can comprise an additional conduit (not shown) which is formed in the body 2 and extends from the collar 3 to the free end 41 of the tubular portion 4. The additional conduit is preferably formed in the upper wall S of the tubular portion 4 in such a way as to be in contact with the back of the pharynx where the secretions accumulate. The additional conduit is coupled to aspiration means in order to remove the secretions.

As is shown in FIGS. 1 to 3, the second auxiliary conduit 7 comprises a bend 71 which connects a first portion 72 of the second auxiliary conduit 7, extending in the longitudinal axis II-II' as far as the second opening 70, and a second portion 73 of the second auxiliary conduit 7 extending in the collar 3. The second portion 73 of the second auxiliary conduit 7 extends in the collar 3 in a radial direction with respect to the longitudinal axis II-II' as far as an output orifice 74.

The upper wall S of the tubular portion 4 has a rounded shape A at the free end 41. The rounded shape A makes it possible to reduce the risks of injury during insertion of the nasopharyngeal cannula 1 into the patient's nostril.

In order to optimize the injection or the extraction of a fluid via an auxiliary conduit 6 or 7, the first auxiliary conduit 6 and the second auxiliary conduit 7 each have a frustoconical shape at the end that opens into the first or second opening 60 or 70. The cross sections of the first opening 60 and of the second opening 70 are therefore larger than the cross sections of the first and second auxiliary conduits 6 and 7, respectively. This frustoconical shape makes it possible to optimize sampling in the case of extraction or to assist the distribution of the fluid injected into the main conduit 5.

The first auxiliary conduit 6 is intended to supply a flow of dioxygen. The second auxiliary conduit 7 is intended to collect a portion of the gases exhaled by the patient, in order to measure the level of carbon dioxide in the gases exhaled by means of a capnograph.

For this purpose, the input orifice 64 and the output orifice 74 are connected respectively to an injection tube 8 and an extraction tube 9 as illustrated in FIG. 1. The connection is produced by welding or by overmolding the collar 3 onto the injection and extraction tubes 8 and 9, or with the aid of connectors.

The free end of the injection tube 8 comprises a specific connector, for example a standard conical connector for dioxygen, which is designed to be coupled to a device delivering a flow of dioxygen, optionally via a tube cross section reducer. By contrast, the free end of the injection tube 9 comprises a specific connector, for example a connector of the Luer lock type, which is designed to be coupled to a capnograph.

As is shown in FIG. 3, the second portion 63 of the first auxiliary conduit 6 and the second portion 73 of the second auxiliary conduit 7 each form an angle α with an axis passing through the first bend 61 and the second bend 62. The angle α has a value of between −10° and 20° and is preferably close to 0°. This angle allows the injection tube 8 and the extraction tube 9 each to be oriented in the direction of the upper edge of an ear of the patient, so as to facilitate the passage of the injection and extraction tubes 8 and 9 behind the ears, as is illustrated in FIG. 7.

Moreover, the second portion 63 of the first auxiliary conduit 6 and the second portion 73 of the second auxiliary conduit 7 can each form an angle of between 0° and 20°, more particularly of about 10°, with the plane defined by the surface of the collar 3, so as to orient the injection and extraction tubes 8 and 9 toward the patient's face and thus optimize the maintenance in position of the nasopharyngeal cannula 1. Since the injection and extraction tubes 8 and 9 are thus brought as close as possible to the patient's face, the risks of an element or a tool getting caught in the tubes are further reduced.

Figure 7:
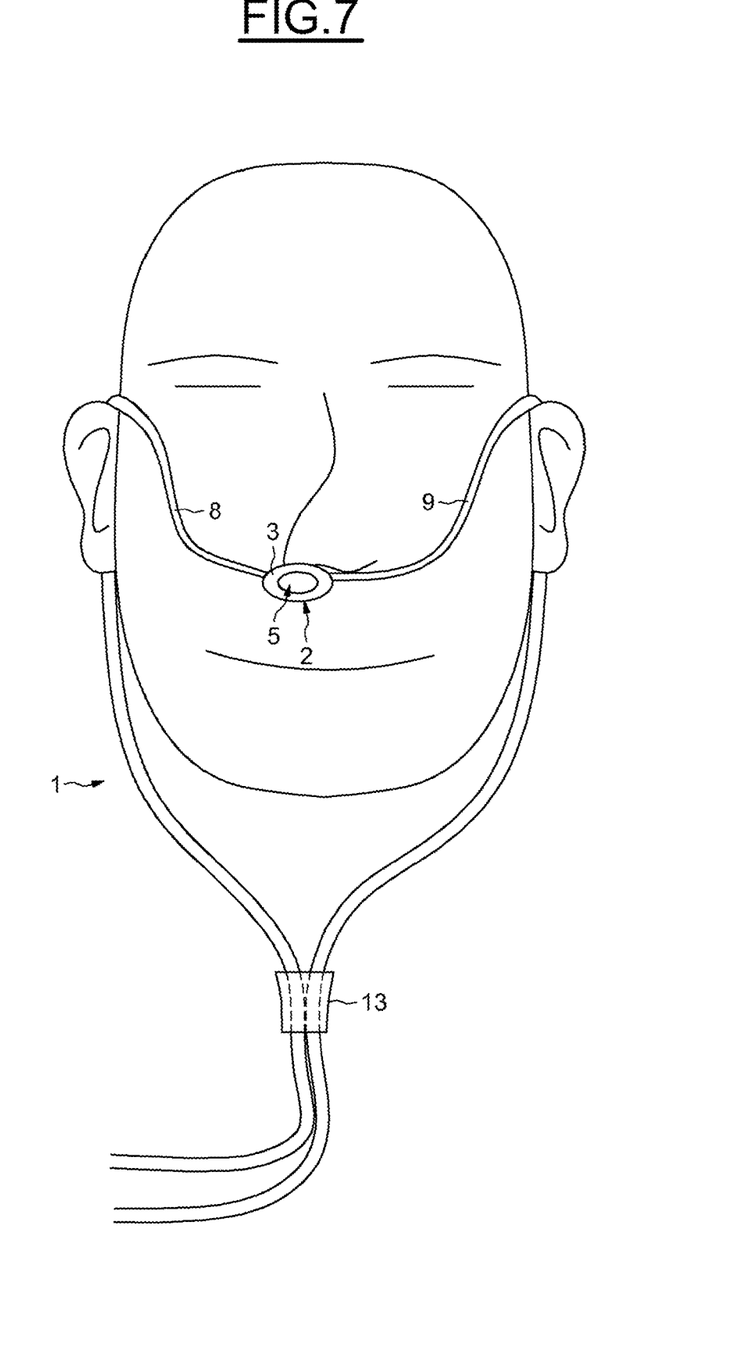
FIG. 7 shows a schematic representation of a nasopharyngeal cannula from FIG. 1 fitted on a patient.

FIG. 7 is a schematic representation of a nasopharyngeal cannula 1 fitted on a patient in accordance with the embodiment of FIG. 1. The passage of the injection and extraction tubes 8 and 9 behind the patient's ears makes it possible to hold the nasopharyngeal cannula 1 in place in the patient's nostril. In this embodiment, the nasopharyngeal cannula 1 additionally comprises a clamping ring 13 which is coupled to the injection and extraction tubes 8 and 9. The clamping ring 13 is mounted so as to slide along the injection and extraction tubes 8 and 9, making it possible to lift the ring 13 until the injection and extraction tubes are clamped under the patient's chin, such that the nasopharyngeal cannula 1 is held securely in position on the patient.

In order to improve the removal of the moisture that is present in the extraction tube 9, the extraction tube can comprise a portion a few centimeters long, 5 cm for example, of Nafion tube. This portion is preferably situated 2 cm from the collar 3.

In an alternative, the first auxiliary conduit 6 formed within the thickness of the body 2 can have a cross section with a curved oblong shape similar to the cross section of the second auxiliary conduit 7. In the case where the two auxiliary conduits 6 and 7 have a curved oblong shape in cross section, the two conduits can extend in the tubular portion 4 in such a way as to be symmetrically opposite the axis of the main conduit 5. Thus, for example, if the second auxiliary conduit 7 is formed in the lower wall I of the tubular portion 4, the first auxiliary conduit 6 can be formed in the upper wall S of the tubular portion.

The proposed invention provides a nasopharyngeal cannula which is able to be fitted and secured quickly on the patient in a removable manner, whilst being held securely in position on the patient. Moreover, the proposed nasopharyngeal cannula is produced as a single piece or is preassembled, such that all that remains is to connect the injection/extraction tubes to the intended appliances. This makes it possible to reduce the fitting time and the risks of connection errors.

The invention claimed is:

1. A nasopharyngeal cannula comprising a body formed by a tubular portion that is curved, and by a collar, the cannula comprising a main conduit forming a fluid passage between the collar and the tubular portion of the body, and two auxiliary conduits which are formed in the body and extend from the collar into the main conduit, characterized in that each auxiliary conduit opens into the collar at an input/output orifice oriented radially with respect to an axis of the main conduit so as to be oriented laterally on each side of a patient's nostril.

2. The cannula as claimed in claim 1, in which a direction between each input/output orifice and an axis of the main conduit forms an angle of between 10° and 20° with an axis orthogonal to the axis of the patient's nose.

3. The cannula as claimed in claim 1, in which the collar comprises an input/output bend for each auxiliary conduit, each auxiliary conduit passing through the collar into the input/output bend opening into the input/output orifice.

4. The cannula as claimed in claim 1, in which each of the two auxiliary conduits comprises a portion formed radially in the collar, the input/output orifice being arranged radially on the collar.

5. The cannula as claimed in claim 4, in which each input/output orifice arranged radially on the collar is connected to an auxiliary conduit via the portion of the auxiliary conduit extending radially in the collar, forming an angle of between 0° and 20° with a plane defined by a surface of the collar, so as to orient a corresponding input/output orifice toward the patient's face.

6. The cannula as claimed in claim 1, comprising two flexible injection/extraction tubes, which are able to be passed behind the patient's ears, a first end of each of the two flexible injection/extraction tubes being connected to an input/output orifice.

7. The cannula as claimed in claim 6, comprising a clamping ring which is able to hold the two flexible injection/extraction tubes together and can slide along the two flexible injection/extraction tubes so as to hold the cannula in place when each of the two flexible injection/extraction tubes passes behind an ear.

8. The cannula as claimed in claim 6, in which a second end of each of the two flexible injection/extraction tubes comprises means for connection to injection appliances.

9. The cannula as claimed in claim 1, in which a first auxiliary conduit comprises an input orifice connected to an injection tube for injecting dioxygen into the patient's airways, and a second auxiliary conduit comprises an output orifice, which is connected to an extraction tube for extracting gases exhaled by the patient so as to perform a capnographic measurement.

10. The cannula as claimed in claim 9, in which the first auxiliary conduit extends as far as a proximal part of the tubular portion, and the second conduit extends as far as a distal part comprising a free end of the tubular portion.

11. The cannula as claimed in claim 9, in which the first auxiliary conduit is formed in an upper wall of the tubular portion of the body, and the second auxiliary conduit is formed in a lower wall of the tubular portion of the body.

12. The cannula as claimed in claim 1, in which at least one of the auxiliary conduits comprises a cross section of oblong shape, at least on the tubular portion of the body.

13. The cannula as claimed in claim 1, in which at least one of the auxiliary conduits comprises an orifice which opens into the main conduit and has a frustoconical shape with a larger cross section than a mean cross section of the auxiliary conduit.

14. The cannula as claimed in claim 10, in which the free end of the tubular portion of the body is provided with a rounded shape.

15. The cannula as claimed in claim 1, in which the body is made of flexible and sliding plastic.

16. The cannula as claimed in claim 2, in which the direction between each input/output orifice and the axis of the main conduit forms an angle of between 0° and 10°, with an axis orthogonal to an axis of the patient's nose.

17. The cannula as claimed in claim 5, in which each input/output orifice arranged radially on the collar is connected to an auxiliary conduit via the portion of the auxiliary conduit extending radially in the collar, forming an angle of about 10°, with the plane defined by the surface of the collar, so as to orient the corresponding input/output orifice toward the patient's face.

* * * * *